(12) United States Patent
Lee et al.

(10) Patent No.: US 7,087,780 B2
(45) Date of Patent: Aug. 8, 2006

(54) PROCESS FOR PRODUCING TETRAKIS($^F$ARYL)BORATE SALTS

(75) Inventors: John Y. Lee, Baton Rouge, LA (US); Rajeev S. Mathur, Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 109 days.

(21) Appl. No.: 10/877,026

(22) Filed: Jun. 24, 2004

(65) Prior Publication Data

US 2004/0230075 A1 Nov. 18, 2004

Related U.S. Application Data

(62) Division of application No. 10/264,475, filed on Oct. 3, 2002, now Pat. No. 6,831,200.

(51) Int. Cl.
*C07F 5/02* (2006.01)
(52) U.S. Cl. .................... 562/7; 568/1; 568/6
(58) Field of Classification Search ............. 562/7; 568/1, 6
See application file for complete search history.

(56) References Cited

U.S. PATENT DOCUMENTS

| | | | |
|---|---|---|---|
| 5,070,161 A | 12/1991 | Nakano et al. | |
| 5,096,936 A | 3/1992 | Seko et al. | |
| 5,223,591 A | 6/1993 | Nyander et al. | |
| 5,340,898 A | 8/1994 | Cavezzan et al. | |
| 5,399,781 A | 3/1995 | Doellein | |
| 5,468,902 A | 11/1995 | Castellanos et al. | |
| 5,514,728 A | 5/1996 | Lamanna et al. | |
| 5,919,983 A | 7/1999 | Rosen et al. | |
| 6,162,950 A | 12/2000 | Lee et al. | |
| 6,169,208 B1 | 1/2001 | Lee | |
| 6,281,389 B1 * | 8/2001 | Mitsui et al. | 568/1 |
| 6,476,271 B1 | 11/2002 | Van der Puy | |
| 6,624,329 B1 | 9/2003 | Mitsui et al. | |
| 2001/0056022 A1 | 12/2001 | Nagata et al. | |

FOREIGN PATENT DOCUMENTS

| | | |
|---|---|---|
| EP | 0331496 A1 | 9/1989 |
| EP | 0913400 A1 | 5/1999 |
| JP | 10316686 | 12/1998 |
| WO | WO 9807798 A1 | 2/1998 |
| WO | WO 9822470 A1 | 5/1998 |

OTHER PUBLICATIONS

Bahr et al.; "Trityl Tetrakis(3,5-bis(trifluoromethyl)phenyl)-borate: A New Hydride Abstraction Reagent"; J. Org. Chem.; 1992; vol. 57; No. 20; pp. 5545-5547.
Brookhart et al.; "[(3,5-(CF$_3$)$_2$C$_6$H$_3$)$_4$B]$^-$[H(OEt$_2$)$_2$]$^+$: A Convenient Reagent for Generation and Stabilization of Cationic, Highly Electrophilic Organometallic Complexes"; Organometallics; vol. 11; 1992; pp. 3920-3922.
Chien et al.; "Isospecific Polymerization of Propylene Catalyzed by *rac*-Ethylenebis(indenyl)-methylzirconium "Cation""; Journal Am. Chem. Soc.; 1991; vol. 113; pp. 8570-8571.
Gol'dberg et al.; "Synthesis of Sodium Tetrakis[3,5-Di(trifluoromethyl)phenyl]borate"; Zhurnal Organicheskoi Khimi; 1989; vol. 25; No. 5; pp. 1099-1102. (Translation thereof); pp. 989-991.
Golden et al.; "Lithium-Mediated Organofluorine Hydrogen Bonding: Structure of Lithium Tetra-kis(3,5-bis(trifluoromethyl)phenyl)borate Tetrahydrate"; Inorg. Chem. vol. 33; No. 24; 1994; p. 5374-5375.
Hayashi et al., "A Novel Chiral Super-Lewis Acidic Catalyst for Enantioselective Synthesis", J. Am. Chem. Soc., 1996, vol. 118, No. 23, pp. 5502-5503.
Jia et al., "Cationic Metallocene Polymerization Catalysts Based on Tetrakis(pentafluorophenyl)-borate and Its Derivatives. Probing the Limits of Anion "Noncoordination" via a Synthetic, Solution Dynamic,Structural, and Catalytic Olefin Polymerization Study", Organometallics, 1997, vol. 16, No. 5; p. 842-857.
Jia et al., "Protected (Fluoroaryl)borates as Effective Counteranions for Cationic Metallocene Polymerization Catalysts", Organometallics, vol. 14, No. 7; 1995; pp. 3135-3137.

(Continued)

*Primary Examiner*—Johann Richter
*Assistant Examiner*—Chukwuma Nwaonicha
(74) *Attorney, Agent, or Firm*—Edgar F. Spielman, Jr.; Marcy M. Hoefling

(57) ABSTRACT

The liquid ethereal medium or liquid hydrocarbyl medium of a solution or slurry of an alkali metal tetrakis($^F$aryl)borate is substituted with at least one halogenated hydrocarbon, without isolating the alkali metal tetrakis($^F$aryl)borate, to form a new slurry or solution. At least a portion of the new solution is mixed together with a salt selected from a) a protic ammonium salt, b) an onium salt, and c) a triarylmethyl salt, to produce a protic ammonium tetrakis($^F$aryl)borate, an onium tetrakis($^F$aryl)borate, or a triarylmethyl tetrakis($^F$aryl)borate.

31 Claims, No Drawings

OTHER PUBLICATIONS

Lancaster, Simon J. et al.; "New Weakly Coordinating Counter Anions for High Activity Polymerisa-tion Catalysts: [$(C_6F_5)_3$B-CN-B$(C_6F_5)_3$]$^-$ and [Ni{CNB$(C_6F_5)_3$}$_4$]$^{2-}$"; J. Chem. Soc. Chem. Comm.; 1999; pp 1533-1534.

Nishida et al., "Tetrakis[3,5-bis(trifluoromethyl)phenyl]borate. Highly Lipophilic Stable Anionic Agent for Solvent-extraction of Cations", Bull Chem. Soc. Jpn., vol. 57, No. 9, 1984, pp. 2600-2604.

Vandeberg et al., "Studies in the Tetraarylborates Part III. The Preparation and Reagent Properties of Sodium Tetrakis(p-Tri-fluoromethylphenyl) Borate and Sodium Tetrakis (m-Fluorophenyl) Borate", Analytica Chimica Acta, Elsevier Publishing Company, Amsterdam,1969, vol. 44, pp. 175-183.

Chemical Abstract, # 15921, line G, Vit, Jaroslav, "Preparaing Sodium Tetraarylborates, esp. Sodium Tetraphenylborate", Organometallic Compounds, vol. 64, 1966, Col. 15921, 1 page.

Chemical Abstract, # 124402W, Wakabayashi et al., "Agrochemical and Industrial Microbicides Containing Tetraphenylborates", 1988, vol. 109, p. 254.

Chemical Abstract, #214696R, Wakabayashi et al., "Pyridinium and Quinolinium Tetraphenylborate Salts as Agrochemical and Industrial Microbicides",Organometallics, 1989, vol. 111, p. 611.

Wittig et al., "Uber Komplexbildung mit Triphenyl-bor (III. Mitt.)", Annalen der Chemie, 1951, vol. 573, pp. 195-209.

Chemical Abstract, # 6607, Line D, Wittig et al., "Complex Formation with Triphenylboron. III.", 1951, vol. 46, 1 page.

"Periodic Table of the Elements", Chem. And Eng. News, Feb. 4, 1985, pp. 26-27.

Liting et al.; Catalyst/Cocatalyst Nuclearity Effects In Single-Site Polymerization. Enhanced Branching and a-Olefin Comonomer Enchainment In Polymerizations Mediated By Binuclear Catalysts and Cocatalysts Via a New Enchainment Pathway; Journal Of The American Chemical Society; vol. 124, No. 43; 2002; pp. 12725-12741.

Kaul et al.; Syntheses and Properties of the Novel Co-Catalysts N,N-dimethylanilimium- and trityl{tetrakis[4-(trifluoromethyl)-2,3,5,6-tetrafluorophenyl]borate}; Journal of Organometllic Chemistry; vol. 621; 2001; pp. 177-183.

* cited by examiner

PROCESS FOR PRODUCING TETRAKIS($^F$ARYL)BORATE SALTS

REFERENCE TO RELATED APPLICATIONS

This application is a division of U.S. application Ser. No. 10/264,475, filed Oct. 3, 2002 now U.S. Pat. No. 6,831,200.

TECHNICAL FIELD

This invention relates to a method for making organic cation tetrakis($^F$aryl)borate salts from an alkali metal tetrakis($^F$aryl)borate. When the organic cation is a protic ammonium cation or a triarylmethyl cation, the tetrakis($^F$aryl) borate salt is useful as a cocatalyst for metallocene-catalyzed polymerization. When the organic cation is an onium cation, the tetrakis($^F$aryl)borate salt is useful as an initiator in the crosslinking of polyorganosiloxanes.

BACKGROUND

It has been found that, when dry, alkali metal tetrakis ($^F$aryl)borates are thermally sensitive. Alkali metal tetrakis ($^F$aryl)borates are also sensitive to shock. These sensitivities clearly indicate potential hazards in the handling and processing of such compounds. Because alkali metal tetrakis ($^F$aryl)borates are useful intermediates in the preparation of organic cation tetrakis($^F$aryl)borates, it would be very desirable to minimize or eliminate these sensitivity problems.

SUMMARY OF THE INVENTION

Surprisingly, it has been discovered that the presence of solvent, especially a halogenated hydrocarbon, mitigates both the thermal and shock sensitivity of alkali metal tetrakis($^F$aryl)borates. Additionally, it has been found that the reaction time when forming triarylmethyl tetrakis($^F$aryl) borates from alkali metal tetrakis($^F$aryl)borates is significantly reduced when operating in halogenated hydrocarbons. In particular, the reaction of 20 grams of potassium tetrakis(pentafluorophenyl)borate with triphenylmethyl chloride is complete in under twenty minutes in dichloromethane, as compared to over ten hours for the same reaction on the same scale in hexane.

An embodiment of this invention is a process for producing protic ammonium tetrakis($^F$aryl)borate, an onium tetrakis($^F$aryl)borate, or a triarylmethyl tetrakis($^F$aryl)borate from a solution or slurry of an alkali metal tetrakis($^F$aryl) borate in a liquid ethereal medium or liquid hydrocarbyl medium. This process comprises substituting the liquid ethereal medium or liquid hydrocarbyl medium with at least one halogenated hydrocarbon, without isolating the alkali metal tetrakis($^F$aryl)borate, to form a new slurry or solution. At least a portion of the new slurry or solution is mixed together with a salt selected from a) a protic ammonium salt, b) an onium salt, and c) a triarylmethyl salt, to produce a protic ammonium tetrakis($^F$aryl)borate, an onium tetrakis ($^F$aryl)borate, or a triarylmethyl tetrakis($^F$aryl)borate. The triarylmethyl cation has three aryl groups bound to a central carbon atom. The protic ammonium cation has the formula $[R_3NH]^\oplus$, in which each R is independently a hydrocarbyl group containing up to about thirty carbon atoms, and the onium cation has the formula $[ER_n]^\oplus$, wherein E is an element of any of Groups 15–17 of the Periodic Table, wherein each R is independently a hydrocarbyl group containing up to about thirty carbon atoms, and wherein n is equal to the valence of E plus one. For labeling of the groups of the Periodic Table, see for example, the Periodic Table appearing in *Chemical & Engineering News*, Feb. 4, 1985, 69, 26.

The borate anion has four fluorine-containing aryl groups, each of which has bonded directly to an aromatic ring at least two fluorine atoms, or at least two perfluorohydrocarbyl groups, or at least one fluorine atom and at least one perfluorohydrocarbyl group. It is preferred that at least two fluorine atoms, or at least two perfluorohydrocarbyl groups are bonded directly to an aromatic ring. Each position on the aromatic ring(s) of the $^F$aryl group that is not a fluorine atom or a perfluorohydrocarbyl group is substituted by a hydrogen atom, a hydrocarbyl group, an alkoxy group, or a silyl group. The $^F$aryl groups may be the same or different from each other; it is preferred that all four $^F$aryl groups are the same.

Further embodiments of this invention will be apparent from the ensuing description and appended claims.

FURTHER DETAILED DESCRIPTION OF THE INVENTION

Liquid ethereal medium is comprised of one or more liquid dihydrocarbyl ethers, and may also include one or more liquid hydrocarbons, water, or mixtures thereof. Liquid hydrocarbyl medium is comprised of one or more liquid hydrocarbons, and may also include one or more liquid dihydrocarbyl ethers, water, or mixtures thereof. Typically, the alkali metal tetrakis($^F$aryl)borate in a liquid ethereal medium is in the form of a solution, while alkali metal tetrakis($^F$aryl)borate in liquid hydrocarbyl medium is usually in the form of a slurry. Often, the alkali metal tetrakis ($^F$aryl)borate in liquid hydrocarbyl medium forms an oily layer at the bottom of the solution when traces of ether and/or water are present.

The alkali metal tetrakis($^F$aryl)borate may be a lithium, sodium, potassium, rubidium, or cesium tetrakis($^F$aryl)borate. Preferably, the alkali metal of the alkali metal tetrakis ($^F$aryl)borate is lithium, potassium, or sodium; most preferably, the alkali metal is sodium or potassium. Most preferred as the alkali metal is potassium; thus, the most preferred alkali metal tetrakis($^F$aryl)borate is a potassium tetrakis ($^F$aryl)borate.

Throughout this document, the term "$^F$aryl group" shall be understood to mean, as described above, a fluorine-containing aryl group, which has bonded directly to an aromatic ring at least two fluorine atoms, or at least two perfluorohydrocarbyl groups, or at least one fluorine atom and at least one perfluorohydrocarbyl group. It is preferred that at least two fluorine atoms or at least two perfluorohydrocarbyl groups are bonded directly to an aromatic ring. Each position on the aromatic ring(s) of the $^F$aryl group that is not a fluorine atom or a perfluorohydrocarbyl group is substituted by a hydrogen atom, a hydrocarbyl group, an alkoxy group, or a silyl group. The aromatic ring of the $^F$aryl group may be, but is not limited to, benzene, naphthalene, anthracene, biphenyl, phenanthrene, or indene. Benzene is the preferred aromatic moiety. The perfluorohydrocarbyl groups include alkyl and aryl perfluorocarbons; suitable perfluorohydrocarbyl groups are, for example, trifluoromethyl, pentafluoroethyl, pentafluorophenyl, and heptafluoronaphthyl. The hydrocarbyl groups of the aryl groups are preferably $C_1$ to $C_{18}$ alkyl groups or $C_6$ to $C_{20}$ aryl or aralkyl groups. Examples of suitable hydrocarbyl groups are methyl, ethyl, isopropyl, tert-butyl, cyclopentyl, methylcyclohexyl, decyl, phenyl, tolyl, xylyl, benzyl, naphthyl, and tetrahydronaphthyl. The alkoxy groups preferably have $C_1$ to $C_6$ alkyl moieties. Some examples of alkoxy groups are methoxy, ethoxy, isopropoxy, methylcyclopentoxy, and cyclohexoxy. The silyl groups preferably have $C_1$ to $C_{18}$ alkyl groups or $C_6$ to $C_{20}$ aryl or aralkyl groups. Suitable silyl groups include trimethylsilyl, triisopropylsilyl, tert-butyl(dimethyl)silyl, tridecylsilyl, and triphenylsilyl. Examples of $^F$aryl groups that may be present on the borate moiety in this invention include 3,5-bis(trifluoromethyl) phenyl, 2,4,6-tris(trifluoromethyl)-phenyl, 4-[tri(isopropyl) silyl]-tetrafluorophenyl, 4-[dimethyl(tert-butyl)silyl]-tetrafluorophenyl, 4'-(methoxy)-octafluorobiphenylyl, 2,3-bis (pentafluoroethyl)-naphthyl, 2-(isopropoxy)-hexafluoronaphthyl, 9,10-bis(heptafluoropropyl)-heptafluoroanthryl, 9,10-bis(p-tolyl)-heptafluorophenanthryl, and 1-(trifluoromethyl)-tetrafluoroindenyl. It is preferred that at most two substituents on the ring of the aryl group are hydrocarbyl, perfluorohydrocarbyl, or alkoxy, while the rest of the substituents are fluorine atoms.

It is highly preferred to have $^F$aryl groups in which the all of the substituents are fluorine atoms. Examples of such groups are pentafluorophenyl, 4-nonafluorobiphenylyl, 2-nonafluorobiphenylyl, 1-heptafluoronaphthyl, 2-heptafluoronaphthyl, 7-nonafluoroanthryl, 9-nonafluorophenanthryl, and analogous groups. The most highly preferred perfluoroaryl group is pentafluorophenyl; thus, the most highly preferred borate is tetrakis(pentafluorophenyl)borate.

Halogenated hydrocarbons that may be used include, but are not limited to, dichloromethane, dibromomethane, trichloromethane, bromochloromethane, dichlorodifluoromethane, 1,2-dichloroethane, 1,2-dibromoethane, tetrachloroethane, 1-bromo-2-chloroethane, trichloroethylene, 1-bromopropane, (chloromethyl)cyclopropane, 1-bromobutane, 1-bromo-2-ethylbutane, 1,1-dichloro-3,3-dimethylbutane, cyclobutyl chloride, neopentyl chloride, 1-bromo-5-chloropentane, cyclopentyl bromide, 1,6-dibromohexane, trans-1,2-dichlorocyclohexane, 1-chloroheptane, 1,8-dichlorooctane, and mixtures of any two or more of the foregoing. Preferred halogenated hydrocarbons are dichloromethane, trichloromethane, and 1,2-dichloroethane; most preferred is dichloromethane.

The substituting of the liquid ethereal medium or liquid hydrocarbyl medium, in which the alkali metal tetrakis ($^F$aryl)borate is dissolved or slurried, with a halogenated hydrocarbon can be accomplished by a variety of means. Typical methods include decantation, solvent exchange via distillation (not to dryness), gentle evaporation (not to dryness), and centrifugation. For example, most of the liquid ethereal or hydrocarbyl medium may be decanted, followed by the addition of the halogenated hydrocarbon(s). If the two media are immiscible, they can be allowed to separate, so that more of the liquid ethereal or liquid hydrocarbyl medium can be decanted. The key is that the alkali metal tetrakis($^F$aryl)borate is not isolated from solvent at any point during the substitution. Generally, a slurry of the the alkali metal tetrakis($^F$aryl)borate in the halogenated hydrocarbon is formed. The substitution can be conducted at any suitable temperature below the boiling point of the halogenated hydrocarbon, so long as the alkali metal tetrakis($^F$aryl)borate is not adversely affected.

The new slurry or solution, comprising the alkali metal tetrakis($^F$aryl)borate in the halogenated hydrocarbon, is mixed with a triarylmethyl salt, protic ammonium salt, or onium salt.

The term "triarylmethyl cation" refers to carbocations which have three aryl groups bound to a central carbon atom. The aryl groups of the triarylmethyl cation have from six to about twenty carbon atoms, can be the same or different, and can be substituted or unsubstituted. Examples of suitable aryl groups include phenyl, tolyl, xylyl, naphthyl, and 2-ethylnaphthyl; preferred are tolyl and phenyl; most preferred is phenyl. The most preferred triarylmethyl cation is a triphenylmethyl cation. Many inorganic anions can be appropriate counterions for a triarylmethyl cation; examples of suitable inorganic anions include chloride, bromide, iodide, tetrafluoroborate, hexafluorophosphate, and the like. Preferred inorganic anions are the halides, especially chloride; thus, the preferred salt is triphenylmethyl chloride.

For the contacting of an alkali metal tetrakis($^F$aryl)borate and a triarylmethyl salt, the halogenated hydrocarbon liquid medium is preferably dry (in the sense of having minimal water present), and it is preferred that the reaction is conducted in an inert atmosphere comprised of one or more inert gases, such as, for example, nitrogen, helium, or argon.

Protic ammonium salts of the tetrakis($^F$aryl)borate can be formed from the alkali metal tetrakis($^F$aryl)borate. These ammonium cations have the general formula $[R_3NH]^\oplus$, wherein each R is independently a hydrocarbyl group containing up to about thirty carbon atoms. R is preferably an aliphatic or aromatic hydrocarbyl group; preferred hydrocarbyl groups include methyl and phenyl. Examples of suitable protic ammonium cations include, but are not limited to, trimethylammonium, triethylammonium, cyclohexyl (dimethyl)ammonium, tri(n-octyl)ammonium, phenyl(dimethyl)ammonium, diphenyl(ethyl)ammonium, and triphenylammonium cations. As described above for the triarylmethyl salt, many inorganic anions can be appropriate counterions for the protic ammonium cation. Again, the halides, especially chloride, are preferred inorganic anions; thus, the preferred salt is generally a protic ammonium chloride.

The protic ammonium salt can be formed shortly before reacting it with the alkali metal tetrakis($^F$aryl)borate; this is accomplished by reacting $R_3N$, wherein R is defined as for the protic ammonium cations, with a protic acid to form the protic ammonium cation. Preferred protic acids include hydrochloric acid, hydrobromic acid, hydroiodic acid, fluoboric acid, and hexafluorophosphoric acid; hydrochloric acid is a particularly preferred protic acid. Preferably, the protic ammonium cation is formed in aqueous solution. For the mixing of the protic ammonium salt and alkali metal tetrakis($^F$aryl)borate, the exclusion of water is not necessary.

Other salts, generally referred to as onium salts, can be reacted with the alkali metal tetrakis($^F$aryl)borate to yield the corresponding onium tetrakis($^F$aryl)borate. Onium cations are defined by the formula $[ER_n]^\oplus$, wherein E is an element of any of Groups 15–17 of the Periodic Table, each R is independently a hydrocarbyl group containing up to about thirty carbon atoms, and n is equal to the valence of E plus one. R is preferably an aliphatic or aromatic hydrocarbyl group. As an example of n, when E is sulfur, which has a valence of two, n is three. As described previously for both the triarylmethyl salts and the protic ammonium salts, many inorganic anions may be appropriate counterions for the onium cation. Preferred inorganic anions are the halides, especially chloride; thus, the preferred salt is generally an onium chloride. To form the onium tetrakis($^F$aryl)borates, standard cation exchange methods can be used. Examples of suitable onium salts include, but are not limited to, diphenyliodonium chloride, tris(p-tolyl)sulfonium bromide, and tetraethylphosphonium chloride.

Generally, the alkali metal tetrakis($^F$aryl)borate and the triarylmethyl salt, protic ammonium salt, or onium salt are mixed together at room temperature. Mixing at room temperature is preferred because the yield of triarylmethyl, protic ammonium, or onium tetrakis($^F$aryl)borate is often much higher than when the mixture is heated. Some heat may be produced during the course of the reaction, raising the temperature of the mixture. The mixture may be heated, provided that the temperature does not exceed the thermal decomposition temperature of the product of the reaction. Heating during contacting of alkali metal tetrakis($^F$aryl)borate and the triarylmethyl, protic ammonium, or onium salt is preferred when a faster reaction rate is desired. Agitation of the reaction mixture is usually necessary for the reaction to proceed.

The contact time for alkali metal tetrakis($^F$aryl)borate and the protic ammonium salt or onium salt is preferably from about fifteen minutes to about eight hours; more preferred is a time in the range of from about twenty minutes to about six hours. For mixing the alkali metal tetrakis($^F$aryl)borate and the triarylmethyl salt, the contact time at room temperature is preferably in the range of from about twenty minutes to about twenty-four hours, and more preferably is in the range of from about one hour to about twelve hours. A contact time for alkali metal tetrakis($^F$aryl)borate and the triarylmethyl salt when heating in the range of from about thirty minutes to about twenty hours is preferred; a more preferable range is from about one hour to about fifteen hours; highly preferred is a contact time in the range of from about two hours to about twelve hours.

Experiments were performed on dry (solvent-free) alkali metal tetrakis($^F$aryl)borates. All materials were tested at "standard" conditions (drop height=100 cm; drop weight=5 kg). Four runs with sodium tetrakis(pentafluorophenyl)borate were performed. A black soot-like char remained in the test cell after testing. Results are summarized in Table 1.

TABLE 1

| Trial | Decomposed | Observations |
| --- | --- | --- |
| 1 | Yes | Residue was mostly discolored (grey/black). No smoke or spark observed. |
| 2 | Yes | Small amount of smoke produced upon impact. Residue was completely discolored (gray/black). |
| 3 | Yes | Residue was completely discolored (grey/black). No smoke or spark observed. |
| 4 | Yes | Sparks and smoke observed upon impact. Black soot-like char residue. |

The following example is presented for purposes of illustration, and is not intended to impose limitations on the scope of this invention.

EXAMPLE

Toluene (0.35 g) was added to 0.72 g of KB($C_6F_5$)$_4$, which resulted in formation of a wet cake. The wet cake could not be stirred. Addition of $CH_2Cl_2$ (2.1 g) to the wet cake resulted in a slurry which was stirrable. Trityl chloride ($Ph_3CCl$; 0.33 g, 120 mol %) was added slowly with stirring into the slurry, forming deep-red $Ph_3CB(C_6F_5)_4$. The slightly exothermic reaction was completed in about 1 minute. KCl was formed as a side product. The KCl was collected by filtration; the filter cake was rinsed with 2.0 g of $CH_2Cl_2$. The resultant solution of $Ph_3CB(C_6F_5)_4$ weighed 4.5 g, for a concentration of 20 wt %. Evaporation of ~1.0 g of $CH_2Cl_2$ gave a 26 wt % of $Ph_3CB(C_6F_5)_4$.

Hexane (~4.0 g) was added slowly to the $Ph_3CB(C_6F_5)_4$/$CH_2Cl_2$ solution at 25° C. with fast stirring. A red oily layer was observed at first; this solidified within 10 minutes and coated the flask wall. After stirring for 1 hour at 25° C., all of the solids came off the flask wall to form fine yellow $Ph_3CB(C_6F_5)_4$ product. This yellow solid was collected by filtration on a coarse frit and then rinsed once with hexane (3.0 g). NMR analysis (internal standard method) of purge-dried B4 solids showed a 99+% purity. The yield was at least 89%.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. Whatever transformations, if any, that occur in situ as a reaction is conducted is what the claim is intended to cover. Thus the fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

The invention claimed is:

1. A process for producing protic ammonium tetrakis($^F$aryl)borate or an onium tetrakis($^F$aryl)borate, from a solution or slurry of an alkali metal tetrakis($^F$aryl)borate in a liquid ethereal medium or a liquid hydrocarbyl medium, which process comprises the steps of:
   i) substituting said liquid ethereal medium or liquid hydrocarbyl medium with at least one halogenated hydrocarbon, without isolating the alkali metal tetrakis($^F$aryl)borate:, to form a new slurry or solution; and
   ii) mixing together at least a portion of said new slurry or solution produced in i) with a salt selected from a) a protic ammonium salt, wherein the protic ammonium cation has the formula [$R_3NH$]⊕, in which each R is independently a hydrocarbyl group containing up to about thirty carbon atoms, and b) an onium salt, wherein the onium cation has the formula [$ER_n$]⊕, wherein E is an element of any of Groups 15–17 of the Periodic Table, wherein each R is independently a hydrocarbyl group containing up to about thirty carbon atoms, and wherein n is equal to the valence of E plus one;

wherein each of the $^F$aryl groups is a fluorine-containing aryl group, each of which has bonded directly to an aromatic ring at least two fluorine atoms, or at least two perfluorohydrocarbyl groups, or at least one fluorine atom and at least one perfluorohydrocarbyl group.

2. A process according to claim 1 wherein said halogenated hydrocarbon is dichloromethane, trichloromethane, or 1,2-dichloroethane.

3. A process according to claim 2 wherein said halogenated hydrocarbon is dichloromethane.

4. A process according to claim 1 wherein said alkali metal tetrakis($^F$aryl)borate is a sodium or potassium tetrakis($^F$aryl)borate.

5. A process according to claim 4 wherein said alkali metal tetrakis($^F$aryl)borate is a potassium tetrakis($^F$aryl)borate.

6. A process according to claim 1 wherein said alkali metal tetrakis($^F$aryl)borate is a sodium or potassium tetrakis($^F$aryl)borate, and wherein said halogenated hydrocarbon is dichloromethane, trichloromethane, or 1,2-dichloroethane.

7. A process according to claim 1 wherein the aromatic ring of said $^F$aryl group is a phenyl ring.

8. A process according to claim 1 wherein all of the positions on said aromatic ring(s) of said aryl group are substituted by fluorine atoms.

9. A process according to claim 8 wherein the tetrakis($^F$aryl)borate is tetrakis(pentafluorophenyl)borate.

10. A process according to claim 9 wherein the alkali metal tetrakis($^F$aryl)borate is sodium tetrakis(pentafluorophenyl)borate or potassium tetrakis(pentafluorophenyl)borate.

11. A process according to claim 1 wherein the alkali metal tetrakis($^F$aryl)borate is sodium tribalism(pentafluorophenyl)borate or potassium tetrakis(pentafluorophenyl)borate, and wherein said halogenated hydrocarbon is dichloromethane, trichloromethane, or 1,2-dichloroethane.

12. A process according to claim 11 wherein the alkali metal tetrakis($^F$aryl)borate is potassium tetrakis(pentafluorophenyl)borate, and wherein said halogenated hydrocarbon is dichloromethane.

13. A process according to claim 1 wherein said salt is a protic ammonium salt.

14. A process according to claim 13 wherein at least one R group of said protic ammonium cation is a phenyl group.

15. A process according to claim 13 wherein the protic ammonium cation is a phenyl(dimethyl)ammonium cation.

16. A process according to claim 13 wherein the protic ammonium cation is a tri(n-octyl)ammonium cation.

17. A process according to claim 1 wherein the alkali metal tetrakis($^F$aryl)borate is sodium tetrakis(pentafluorophenyl)borate or potassium tetrakis(pentafluorophenyl)borate, and wherein said salt is a protic ammonium salt.

18. A process according to claim 17 wherein at least one R group of said protic ammonium cation is a phenyl group.

19. A process according to claim 17 wherein the protic ammonium cation is a phenyl(dimethyl)ammonium cation.

20. A process according to claim 17 wherein the protic ammonium cation is a tri(n-octyl)ammonium cation.

21. A process according to claim 1 wherein the alkali metal tetrakis($^F$aryl)borate is sodium tetrakis(pentafluorophenyl)borate or potassium tetrakis(pentafluorophenyl)borate, wherein said halogenated hydrocarbon is dichloromethane, trichloromethane, or 1,2-dichloroethane, wherein said salt is a protic ammonium salt, and wherein the protic ammonium cation is a phenyl(dimethyl)ammonium cation.

22. A process according to claim 1 wherein the alkali metal tetrakis($^F$aryl)borate is sodium tetrakis(pentafluorophenyl)borate or potassium tetrakis(pentafluorophenyl)borate, wherein said halogenated hydrocarbon is dichloromethane, trichloromethane, or 1,2-dichloroethane, wherein said salt is a protic ammonium salt, and wherein the protic ammonium cation is a tri(n-octyl)ammonium cation.

23. A process according to claim 1 wherein said salt is an onium salt.

24. A process according to claim 23 wherein at least one R group of said onium cation is a phenyl group.

25. A process according to claim 22 wherein all of the R groups of said onium cation are the same.

26. A process according to claim 24 wherein said onium salt is a diphenyliodonium salt.

27. A process according to claim 1 wherein the alkali metal tetrakis($^F$aryl)borate is sodium tetrakis(pentafluorophenyl)borate or potassium tetrakis(pentafluorophenyl)borate, and wherein said salt is an onium salt.

28. A process according to claim 27 wherein at least one R group of said onium cation is a phenyl group.

29. A process according to claim 27 wherein said onium salt is a diphenyliodonium salt.

30. A process according to claim 1 wherein the alkali metal tetrakis($^F$aryl)borate is sodium tetrakis(pentafluorophenyl)borate or potassium tetrakis(pentafluorophenyl)borate, wherein said halogenated hydrocarbon is dichloromethane, trichloromethane, or 1,2-dichloroethane, wherein said salt is an onium salt, and wherein said onium salt is a diphenyliodonium salt.

31. A process according to claim 1 wherein said at least a portion of alkali metal tetrakis($^F$aryl)borate and said salt are at room temperature when mixed together.

* * * * *

UNITED STATES PATENT AND TRADEMARK OFFICE
CERTIFICATE OF CORRECTION

PATENT NO. : 7,087,780 B2  Page 1 of 1
APPLICATION NO. : 10/877026
DATED : August 8, 2006
INVENTOR(S) : Lee et al.

It is certified that error appears in the above-identified patent and that said Letters Patent is hereby corrected as shown below:

Column 7, line 37 reads "tribalism" and should read -- tetrakis --.

Signed and Sealed this

Sixth Day of January, 2009

JON W. DUDAS
*Director of the United States Patent and Trademark Office*